(12) United States Patent
Yuds et al.

(10) Patent No.: US 11,295,857 B1
(45) Date of Patent: Apr. 5, 2022

(54) CONNECTED HEALTH SYSTEM HAVING AN INSTANT USER FEEDBACK INTERFACE

(71) Applicants: Fresenius Medical Care Holdings, Inc., Waltham, MA (US); Fresenius Medical Care Deutschland GmbH, Bad Homburg (DE)

(72) Inventors: David Yuds, Hudson, NH (US); Manuel Hassler, Oberursel (DE); Jessica Steuber, Ashland, MA (US); Harshavardhana Reddy Mallipalli, San Ramon, CA (US)

(73) Assignees: Fresenius Medical Care Deutschland GmbH, Bad Homburg (DE); Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 17/217,586

(22) Filed: Mar. 30, 2021

(51) Int. Cl.
| | |
|---|---|
| *G06F 3/16* | (2006.01) |
| *G16H 40/67* | (2018.01) |
| *G06F 3/02* | (2006.01) |
| *G16H 20/40* | (2018.01) |
| *H04L 12/66* | (2006.01) |
| *G16H 80/00* | (2018.01) |
| *G06F 3/0482* | (2013.01) |

(52) U.S. Cl.
CPC ............... *G16H 40/67* (2018.01); *G06F 3/02* (2013.01); *G06F 3/0482* (2013.01); *G06F 3/167* (2013.01); *G16H 20/40* (2018.01); *G16H 80/00* (2018.01); *H04L 12/66* (2013.01)

(58) Field of Classification Search
CPC combination set(s) only.
See application file for complete search history.

(56) References Cited

U.S. PATENT DOCUMENTS

| | | | |
|---|---|---|---|
| 8,323,503 | B2 | 12/2012 | Levin et al. |
| 8,632,485 | B2 | 1/2014 | Schlaeper et al. |
| 8,698,741 | B1 | 4/2014 | Wang et al. |
| 8,924,458 | B2 | 12/2014 | Levin et al. |
| 9,514,283 | B2 | 12/2016 | Childers et al. |
| 9,839,735 | B2 * | 12/2017 | Tanenbaum ........... G16H 20/40 |
| 10,288,881 | B2 | 5/2019 | Christensen |
| 10,441,696 | B2 | 10/2019 | Tanenbaum et al. |
| 11,031,128 | B2 | 6/2021 | Plahey et al. |
| 2014/0257003 | A1 | 9/2014 | Tschirschwitz et al. |

(Continued)

*Primary Examiner* — Hien L Duong
(74) *Attorney, Agent, or Firm* — Fish & Richardson P.C.

(57) ABSTRACT

A connected health system includes an instant user feedback interface that captures meaningful feedback from medical patients, such as dialysis patients, when they are most apt to provide it. The system enables a patient to speak freely with comments or questions about their dialysis experience at the time that the comments or questions arise. Accordingly, the system described herein facilitates and invites the providing of user feedback by voice input, along with relevant treatment and system status information, in a secure way to improve user experience and to help in machine development using simple and easily accessible interface buttons. By providing a conduit for instant user feedback, that may be provided along with relevant treatment and/or system status information that has caused the user feedback, the system described herein may improve the way the patient feels about interactions with the company and their dialysis machines and services.

18 Claims, 9 Drawing Sheets

(56) References Cited

U.S. PATENT DOCUMENTS

| | | |
|---|---|---|
| 2015/0347367 A1* | 12/2015 | Berke .................... G06F 40/169 |
| | | 715/771 |
| 2016/0206800 A1 | 7/2016 | Tanenbaum et al. |
| 2017/0048585 A1* | 2/2017 | Dong ....................... G06F 3/167 |
| 2017/0168688 A1 | 6/2017 | Yuds |
| 2017/0186301 A1* | 6/2017 | Vaddepally ............. H04L 67/12 |
| 2017/0221336 A1* | 8/2017 | Ogaz .................. G08B 21/0423 |
| 2019/0209764 A1* | 7/2019 | Buraczenski .......... G16H 40/20 |
| 2019/0327584 A1 | 10/2019 | Plahey et al. |
| 2021/0093764 A1 | 4/2021 | Merics et al. |

* cited by examiner

CONNECTED HEALTH SYSTEM HAVING AN INSTANT USER FEEDBACK INTERFACE

TECHNICAL FIELD

This application relates generally to systems and methods for providing an instant user feedback interface for medical devices, such as dialysis machines, in a connected health system.

BACKGROUND

Medical devices, such as dialysis machines, are known for use in the treatment of renal disease. The two principal dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. During peritoneal dialysis, the patient's peritoneal cavity is periodically infused with dialysate, or dialysis solution. The membranous lining of the patient's peritoneum acts as a natural semi-permeable membrane that allows diffusion and osmosis exchanges to take place between the solution and the blood stream. Automated peritoneal dialysis machines, also called PD cyclers, are designed to control the entire peritoneal dialysis process so that it can be performed at home, usually overnight, without clinical staff in attendance. Both HD and PD machines may include displays with touch screens or other user interfaces that display information of a dialysis treatment and/or enable an operator or patient to interact with the machine.

Dialysis treatments performed in the home, which may include PD and/or home HD treatments, may be monitored remotely by clinicians and medical device companies through connection to a network modem or gateway that may be part of a secure connected health system. The patient's treatment data may be collected along with status of the dialysis machine. The status may include a variety of details like alarm occurrences, power failure events, software version status, and even location information. This personal health information (PHI) is encrypted and, when analyzed using data analytics, anonymized to protect the patient's identity. The clinician has access to the patient's PHI via the connected health system and may use it to understand the efficacy of the treatments, discussing it with the patient either by telehealth visits (phone or video conference) or in person during the patient's scheduled clinic visits. If the patient has a concern with their dialysis device, they can discuss it at this time. Additionally, patients may call the dialysis device manufacturer's hotline to report any concerns with the equipment. Both the clinic visit and the hotline paths allow the patient to provide useful feedback to dialysis device manufacturers on how to improve their devices.

There is often a period of time between visits with a patient's clinician during which a patient may either forget a concern about the device or may believe that reporting the concern has diminished in importance. Additionally, receiving feedback via the dialysis manufacturer's hotline has a different hurdle: the required actions of having to contact the dialysis manufacturer may be enough of an obstacle to cause the user to avoid this option for providing feedback. Accordingly, as a result, unless the feedback is related to a health risk or a device failure, the patient may find it is easier to simply dismiss their own concerns and deal with the issue without reporting a problem. This may be especially true where the feedback issue occurs at night during a nocturnal dialysis treatment when all the patient wants to do is resolve the issue and go back to sleep. By the next day, the concern may be forgotten or dismissed, resulting in a limitation for patients in being able to provide feedback and preventing the clinicians and/or device manufacturers from receiving valuable patient feedback.

Accordingly, it would be desirable to provide a system that addresses the above-noted concerns and other issues.

SUMMARY

According to the system described herein, an instant user feedback system is provided for a medical device in a home. The system includes a gateway device configured to connect to a local network within the home and configured to connect to a remote network that is external to the home. A microphone is configured to receive voice input from a user. An instant user feedback interface is communicatively coupled to the gateway device, wherein, when engaged, the instant user feedback interface activates the microphone to receive the voice input from the user. The gateway device includes a control unit that is configured to: process the voice input into transmissible user feedback information; obtain status information of the medical device via the local network; and transmit the user feedback information and the status information to a remote system via the external network.

According further to the system described herein, a medical system includes a medical device disposed in a home of a user and an instant user feedback system for the medical device, an instant user feedback system is provided for a medical device in a home. The instant user feedback system includes a gateway device configured to connect to a local network within the home and configured to connect to a remote network that is external to the home. A microphone is configured to receive voice input from a user. An instant user feedback interface is communicatively coupled to the gateway device, wherein, when engaged, the instant user feedback interface activates the microphone to receive the voice input from the user. The gateway device includes a control unit that is configured to: process the voice input into transmissible user feedback information; obtain status information of the medical device via the local network; and transmit the user feedback information and the status information to a remote system via the external network.

According to aspects of the system described herein, multiple feature implementations may be provided in connection with the instant user feedback system and medical system described herein. The medical device may be a dialysis machine. The instant user feedback interface may include a button on the gateway device and/or the instant user feedback interface may include a button on a user feedback device that is remote from the gateway device and that communicates with the gateway device. The gateway device may comprise a speaker configured to output spoken words to the user. The gateway device may be configured to provide two-way conversational capability between the user and the gateway device. The instant user feedback interface may include two buttons that present two options to the user, wherein a first option of the two options is an identification option that indicates user identification information will be transmitted identifying the user, and wherein a second option of the two options is a non-identification option that indicates limited user identification information will be transmitted. The non-identification option may include safety protocol information that enables emergency condition identification of the user. A responsive action in response to the user feedback information may be determined at the remote system, and the instant user feedback system may receive information on the responsive action from the remote system. The system may further comprise a mobile computing device of the user that couples to the gateway device when brought into proximity to the gateway device and that is configured to provide an image or a video to the gateway device related to the voice input.

BRIEF DESCRIPTION OF THE DRAWINGS

Implementations and features of the system described herein are explained with reference to the several figures of the drawings, which are briefly described as follows.

DETAILED DESCRIPTION

Figure 1A:
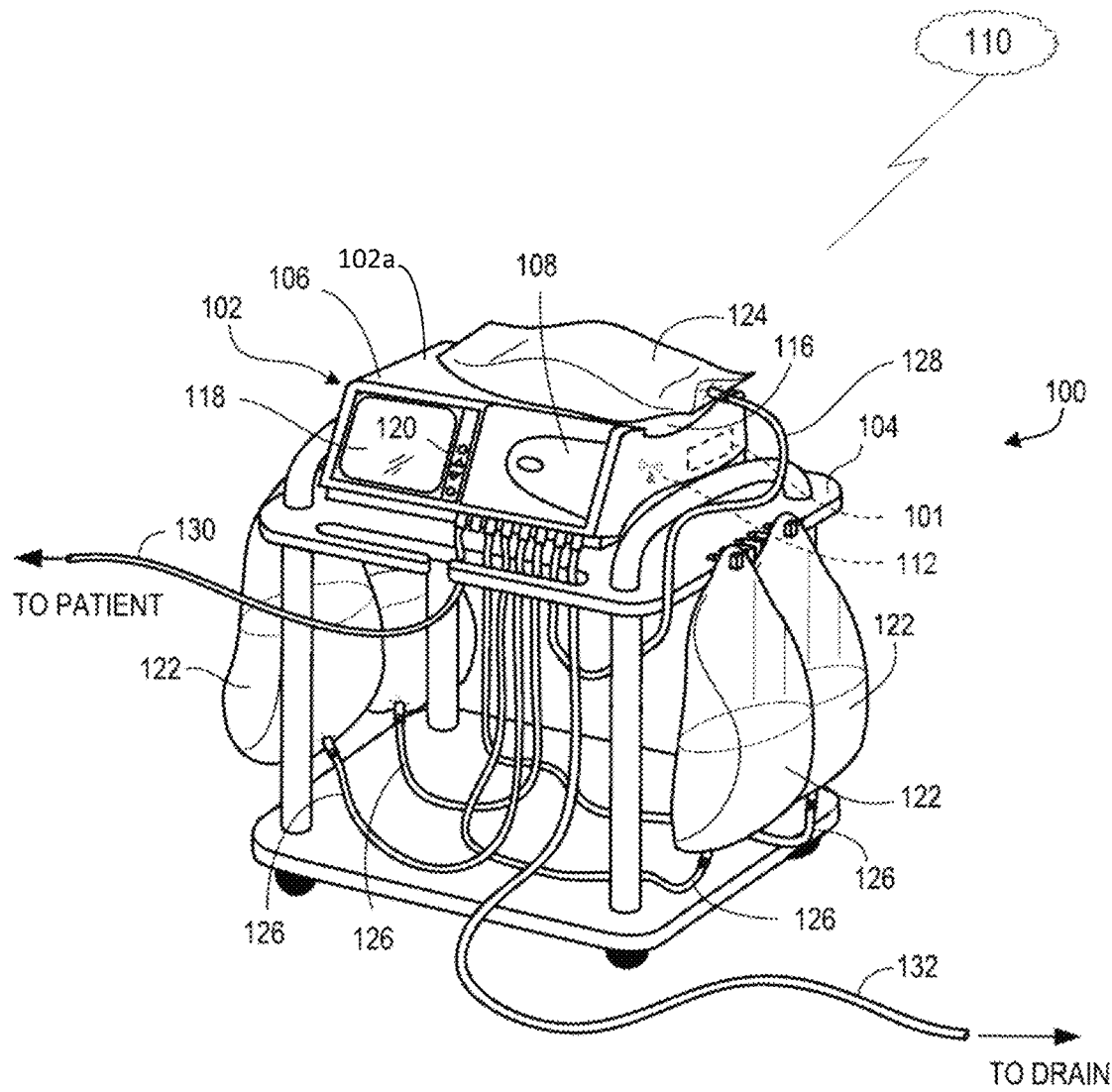
FIG. 1A illustrates an exemplary implementation of a dialysis machine in a dialysis system configured for use in accordance with the present disclosure.

FIG. 1A shows an example of a medical device, implemented as a peritoneal dialysis (PD) system 100, that is configured for use in accordance with an exemplary implementation of the system described herein. In some implementations, the PD system 100 may be configured for use at a patient's home (e.g., a home dialysis system). The PD system 100 may include a dialysis machine 102 (e.g. a PD machine, also referred to as a PD cycler) which in some embodiments may be seated on a cart 104. The dialysis machine 102 may include a housing 106, a door 108, and a cartridge interface for contacting a disposable PD cassette, or cartridge, when the cartridge is disposed within a compartment formed between the cartridge interface and the closed door 108. A heater tray 116 may be positioned on top 102a of the housing 106. The heater tray 116 may be any size and shape to accommodate a bag of dialysate (e.g., a 5 L bag of dialysate). The dialysis machine 102 may also include a user interface such as a touch screen 118 and control panel 120 operable by a user (e.g., a caregiver or a patient) to allow, for example, set up, initiation, and/or termination of a PD treatment.

Dialysate bags 122 may be suspended from the sides of the cart 104, and a heater bag 124 may be positioned in the heater tray 116. Hanging the dialysate bags 122 may improve air management as any air is disposed by gravity to a top portion of the dialysate bag 122. Valves may be attached to a bottom portion of the dialysate bags 122 so fluid is drawn out and air delivery is minimized. Dialysate from the dialysate bags 122 may be transferred to the heater bag 124 in batches. For example, a batch of dialysate may be transferred from the dialysate bags 122 to the heater bag 124, where the dialysate is heated by the heating element. When the batch of dialysate has reached a predetermined temperature (e.g., approximately 98°–100° F., 37° C.), the batch of dialysate may be flowed into the patient. The dialysate bags 122 and the heater bag 124 may be connected to the cartridge via dialysate bag lines 126 and a heater bag line 128, respectively. The dialysate bag lines 126 may be used to pass dialysate from dialysate bags 122 to the cartridge during use, and the heater bag line 128 may be used to pass dialysate back and forth between the cartridge and the heater bag 124 during use. In addition, a patient line 130 and a drain line 132 may be connected to the cartridge. The patient line 130 may be connected to a patient's abdomen via a catheter and may be used to pass dialysate back and forth between the cartridge and the patient's peritoneal cavity during use. The drain line 132 may be connected to a drain or drain receptacle and may be used to pass dialysate from the cartridge to the drain or drain receptacle during use.

The touch screen 118 and the control panel 120 may allow a user to input various treatment parameters to the dialysis machine 102 and to otherwise control the dialysis machine 102. In addition, the touch screen 118 may serve as a display. The touch screen 118 may function to provide information to the patient and the operator of the PD system 100. For example, the touch screen 118 may display information related to a dialysis treatment to be applied to the patient, including information related to a prescription. In various embodiments, the control panel 120 may also include audio and video component capabilities, including speakers, microphones and/or cameras.

The dialysis machine 102 may include a processing module 101 that resides inside the dialysis machine 102, the processing module 101 being configured to communicate with the touch screen 118 and the control panel 120. The processing module 101 may be configured to receive data from the touch screen 118 the control panel 120 and sensors, e.g., temperature and pressure sensors, and control the dialysis machine 102 based on the received data. For example, the processing module 101 may adjust the operating parameters of the dialysis machine 102.

The dialysis machine 102 may be configured to connect to a network 110. The connection to network 110 may be via a wireless connection, such as via WiFi or Bluetooth, or in some cases a non-wireless connection, as further discussed elsewhere herein. The dialysis machine 102 may include a connection component 112 configured to facilitate the connection to the network 110. The connection component 112 may be a transceiver for wireless connections and/or other signal processor for processing signals transmitted and received over a wired connection. In the case of a wired connection, the connection component 112 may be a port enabling a physical connection to a network component. Other medical devices (e.g., other dialysis machines) or components may be configured to connect to the network 110 and communicate with the dialysis machine 102.

Although discussed herein principally in connection with a peritoneal dialysis machine, the system described herein may be used and implemented in connection with other types of medical devices having one or more displays, including home hemodialysis machines and/or other home medical devices.

Figure 1B:
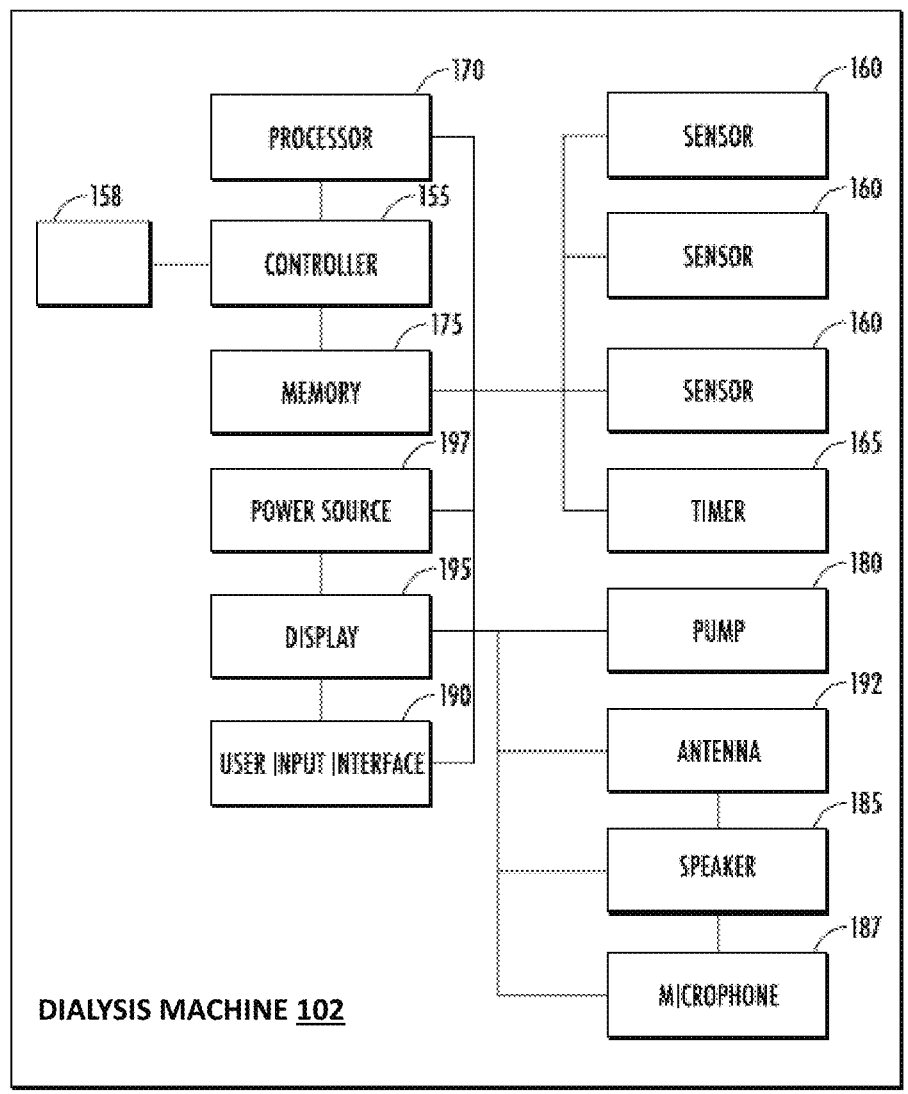
FIG. 1B is a schematic illustration of an exemplary embodiment of the dialysis machine that is configured for use in accordance with the present disclosure.

FIG. 1B is a schematic illustration of an exemplary embodiment of a dialysis machine such as, for example, the dialysis machine 102 that is configured for use in accordance with the present disclosure. The machine 102 may be a home dialysis machine, e.g., a PD machine, for performing a dialysis treatment on a patient, and may be included in the system 100 described above. A controller 155, that may be a component of the processing module 101, may automatically control execution of a treatment function during a course of dialysis treatment. The controller 155 may be operatively connected to the sensors 160 and deliver a signal to execute a treatment function or a course of treatment associated with various treatment systems. In some embodiments, a timer 165 may be included for timing triggering of the sensors 160.

In some embodiments, the machine 102 may also include a processor 170, and memory 175, the controller 155, the processor 170, and/or the memory 175, or combinations thereof, that may separately or collectively part of the processing module 101, that may receive signals from the sensor(s) 160 indicating various parameters. Each fluid bag (e.g., the dialysate bags 122) may contain an approximate amount of dialysate, such that "approximate amount" may be defined as a 3 L fluid bag containing 3000 to 3150 mL, a 5 L fluid bag containing 5000 to 5250 mL, and a 6 L fluid bag containing 6000 to 6300 mL. The controller 155 may also detect connection of all fluid bags 122 connected.

Communication between the controller 155 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pumps and/or compressors to deliver dialysate and the like) and a status associated with specific operations (e.g., ready to execute, executing, completed, successfully completed, queued for execution, waiting for control signal, and the like).

In some embodiments, the dialysis machine 102 may include at least one pump 180 operatively connected to the controller 155. During a treatment operation, the controller 155 may control the pump 180 for pumping fluid, e.g., fresh and spent dialysate, to and from a patient. For example, the pump 180 may transfer dialysate from the dialysate bag 122 through, for example, a cassette insertable into a port formed in the dialysis machine, to the heating to chamber 152 prior to transferring the dialysis to the patient. In an embodiment, the pump 180 may be a peristaltic pump. The controller 155 may also be operatively connected to a speaker 185 and a microphone 187 disposed in the machine 102. A user input interface 190 may include a combination of hardware and software components that allow the controller 155 to communicate with an external entity, such as a patient, caregiver or other user. These components may be configured to receive information from actions such as physical movement or gestures and verbal intonation. In some embodiments, the components of the user input interface 190 may provide information to external entities. Examples of the components that may be employed within the user input interface 190 include keypads, buttons, microphones, touch screens, gesture recognition devices, display screens, and speakers. The machine 102 may also be wirelessly connectable via an antenna 192 for remote communication that may be a part of the connection component 112. The machine 102 may also include a display 195 and a power source 197.

The sensors 160 may be included for monitoring parameters and may be operatively connected to at least the controller 155, the processor 170, and/or the memory 175, or combinations thereof. The processor 170 may be configured to execute an operating system, which may provide platform services to application software, e.g., for operating the dialysis machine 102. These platform services may include inter-process and network communication, file system management and standard database manipulation. One or more of many operating systems may be used, and examples are not limited to any particular operating system or operating system characteristic.

The memory 175 may include a computer readable and writeable nonvolatile data storage medium configured to store non-transitory instructions and data. In addition, the memory 175 may include a processor memory that stores data during operation of the processor 170. In some examples, the processor memory includes a relatively high performance, volatile, random access memory such as dynamic random-access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 175 may include executable programs or other code that may be executed by the processor 170. The instructions may be persistently stored as encoded signals, and the instructions may cause the processor 170 to perform the functions described herein. The memory 175 may include information that is recorded, on or in, the medium, and this information may be processed by the processor 170 during execution of instructions. The memory 175 may also include, for example, specification of data records for user timing requirements, timing for treatment and/or operations, historic sensor information, and the like. The medium may, for example, be optical disk, magnetic disk or flash memory, among others, and may be permanently affixed to, or removable from, the controller 155.

The sensor(s) 160 may include a pressure sensor for monitoring fluid pressure of the machine 102, although the sensors 160 may also include any of a heart rate sensor, a respiration sensor, a temperature sensor, a weight sensor, an air sensor, a video sensor, a thermal imaging sensor, an electroencephalogram sensor, a motion sensor, an audio sensor, an accelerometer, a capacitance sensor, or any other suitable sensor. It is appreciated that the sensors 160 may include sensors with varying sampling rates, including wireless sensors.

The controller 155 may be disposed in the machine 102 or may be coupled to the machine 102 via a communication port or wireless communication links, shown schematically as communication element 158 that may be a part of the connection component 112. According to various examples, the communication element 158 may support a variety of one or more standards and protocols, examples of which include wireless and/or non-wireless communication, such as USB, Wi-Fi, TCP/IP, Ethernet, Bluetooth, among others. As a component disposed within the machine 102, the controller 155 may be operatively connected to any of the sensors 160, the pump 180, and the like. The controller 155 may communicate control signals or triggering voltages to the components of the machine 102. As discussed, exemplary embodiments of the controller 155 may include wireless communication interfaces. The controller 155 may detect remote devices to determine if any remote sensors are available to augment any sensor data being used to evaluate the patient.

Figure 2:
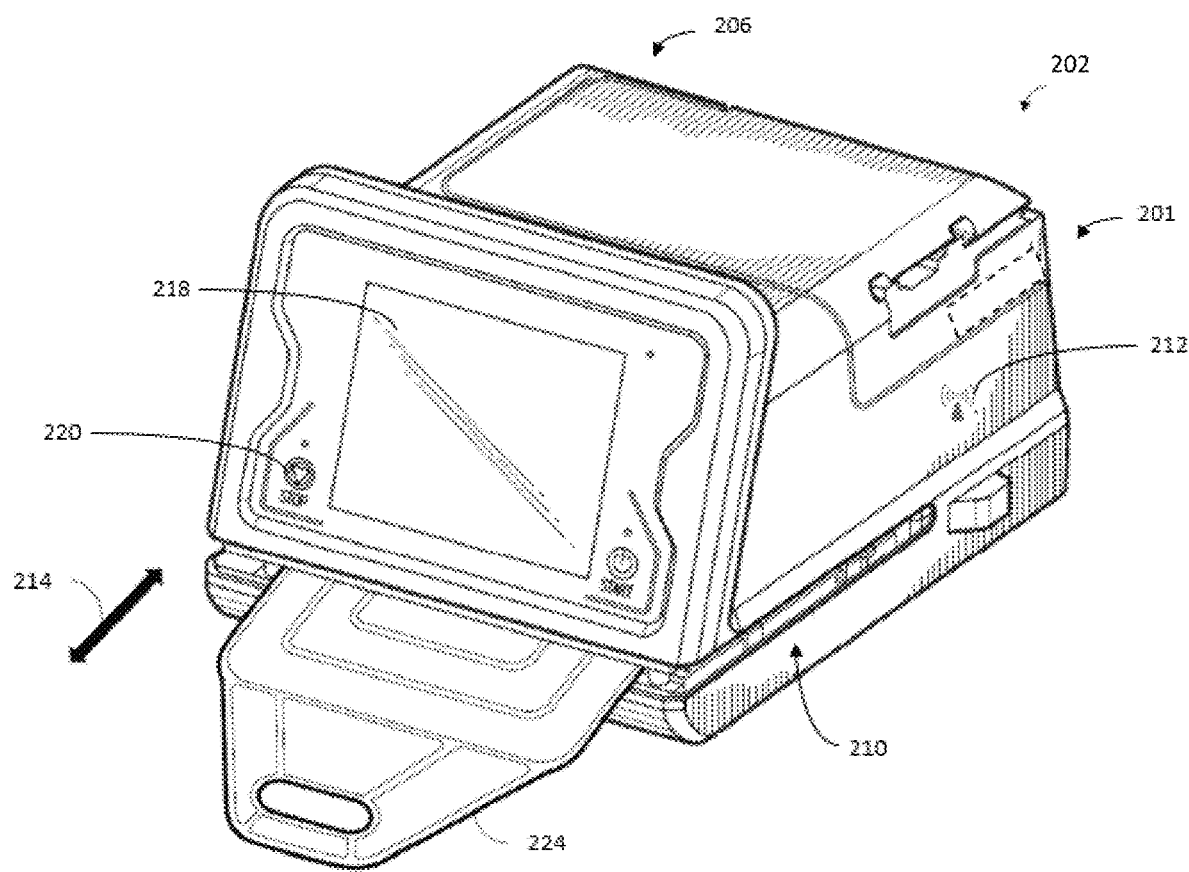
FIG. 2 illustrates another exemplary implementation of a dialysis machine that is configured for use in accordance with the present disclosure.

FIG. 2 is a schematic illustration showing another exemplary embodiment of a dialysis machine 202 in accordance with the present disclosure. The dialysis machine 202 may be implemented in the peritoneal dialysis system 100 and may have at least some similar components as that of the dialysis machine 102, for example, including a housing 206, a processing module 201, a connection component 212, a touch screen 218, and a control panel 220 operable by a user (e.g., a caregiver or a patient) to allow, for example, set up, initiation, and/or termination of a PD treatment. The processing module 201 and the connection component 212 may be configured similarly to the processing module 101 and connection component 112 described above. However, instead of a heater tray being positioned on a top surface 102a of the housing as shown for the dialysis machine 102, one or more heating elements may be disposed internal to the machine 202. For example, a warmer pouch 224 may be insertable into an opening 210 in a direction indicated at arrow 214. In embodiments, the warmer pouch 224 may be configured so dialysate may continually flow through the warmer pouch (instead of transferred in batches) to achieve a predetermined temperature before flowing into the patient.

The connection component 112, 212 may provide for connection of the dialysis machine 102, 202 through a secure gateway to connect to the network, including a network within the home and/or outside the home to send and receive information between devices and/or to a clinic. The connection, network and data transmissions among components, both local and external, may be controlled and/other otherwise incorporated into a system that facilitates such functions with appropriate network infrastructure, and which may, in some implementations, be referred to as a connected health system.

Figure 3:
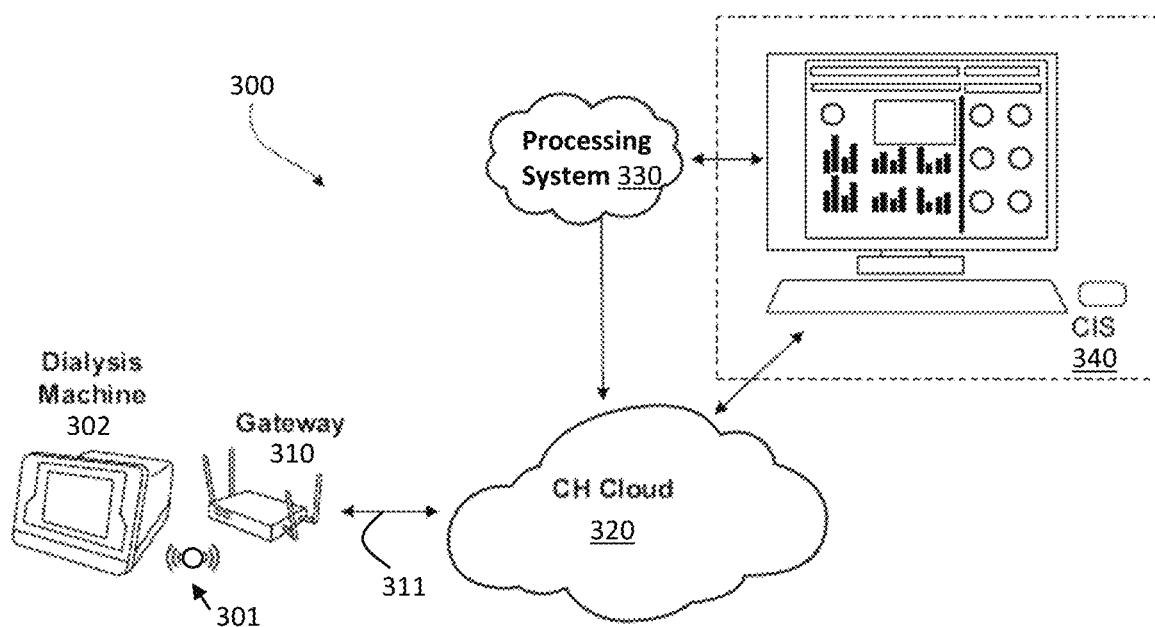
FIG. 3 is a schematic illustration showing an example of a connected health (CH) system that may include, among other things, a processing system, a CH cloud, and a gateway device that may be used in connection with the system described herein.

FIG. 3 is a schematic illustration showing an example of a connected health (CH) system 300 that may include, among other things, a gateway device 310 and a CH cloud service 320. The CH system 300 may provide for communication and/or connectivity of a dialysis machine 302, that may be similar to one or more of the dialysis machines 102, 202 discussed elsewhere herein and/or may include a different type of dialysis machine, such as a home HD machine. Via the CH system 300, the dialysis machine 302 may be connected to internal and external networks, including with remote servers and/or entities. The gateway device 310 may serve as a communication device facilitating communication among components of the CH system 300. The CH cloud 320 may be a cloud-based application or service (e.g. Software as a Service) implementation that serves as a communication pipeline that facilitates the transfer of data among components of the CH system 300 via connections to a network such as the Internet. A processing system 330 may be a server and/or cloud-based system that processes, compatibility checks and/or formats medical information, including prescription information generated at a clinical information system (CIS) 340 of a clinic or hospital, in connection with data transmission operations of the CH system 300. The CH system 300 may include appropriate encryption and data security mechanisms.

In various embodiments, the gateway device 310 is in communication with the dialysis machine 302 via a wireless connection 301, which may be done over a short range network, such as Bluetooth, Wi-Fi and/or other appropriate type of local or short range wireless connection. The gateway 310 may also be in connection with the CH cloud 310 via an external network (e.g. the Internet) connection 311. The gateway device 310 is configured to transmit/receive data to/from the CH cloud 320 and transmit/receive data to/from the dialysis machine 302. In various implementations, the dialysis machine 302 may poll the CH cloud 320 for available files (e.g., via the gateway device 310), and the dialysis machine 302 may temporarily store available files for processing.

According to the system described herein, a connected health system includes an instant user feedback interface that provides hardware and/or software systems to capture meaningful, instant feedback from dialysis patients when they are most apt to provide it. As used herein, "instant," in connection to user feedback, refers to a substantially contemporaneous time period to the occurrence of an identified issue by a patient or desire by that patient to provide feedback. In one or more implementations, the period of time for "instant" feedback may depend on a context of the medical device setup or status of the treatment being performed. For example, whereas during setup of a dialysis treatment or dialysis machine, a patient may not yet be undergoing treatment and thereby immediately able to activate the instant user feedback interface described herein, such as within a minute of the desire to provide user feedback. Additionally and/or alternatively, for a user feedback desire that occurs at the beginning of a treatment (such as a home HD treatment), the patient may need to wait until the dialysis treatment is completed before engaging the instant user feedback interface, which may, for example, be a period of a few hours. For example, the instant feedback may be provided within: a minute, 10 minutes, 1 hour and/or 4 hours, depending on the type or status of the treatment and/or the configuration of the system. In any event, the instant user feedback interface described herein enables the patients to speak freely with comments or questions about the dialysis experience at the moment of, or within a short time period therefrom, that the feedback arises to the patient.

Accordingly, the system described herein facilitates and invites the providing of user feedback by voice input, along with relevant treatment and system status information, in a secure way to improve user experience and to help in machine development using simple and easily accessible interface buttons. By providing a conduit for instant user feedback, that may be provided along with relevant treatment and/or system status information that has caused the user feedback, the system described herein may improve the way the patient feels about interactions with the company and their dialysis machines and services.

Figure 4:
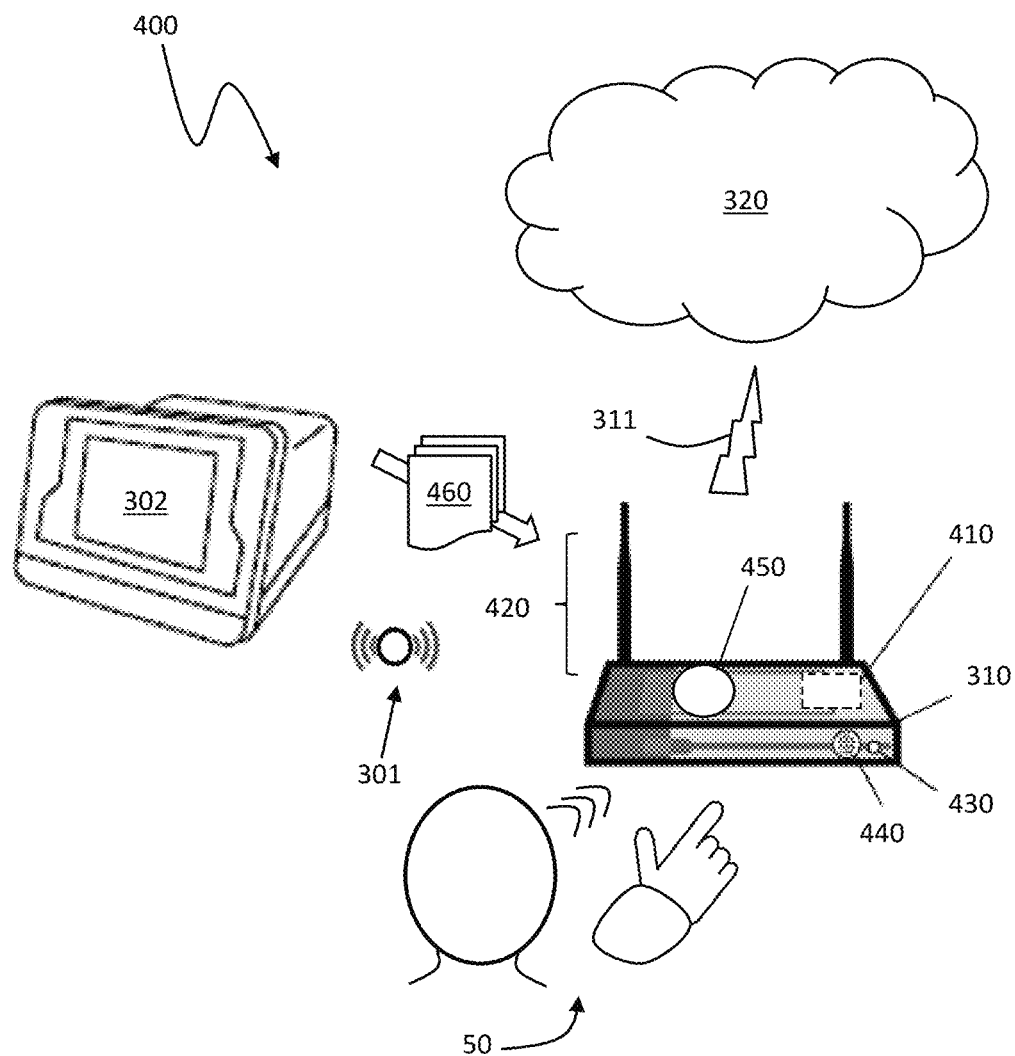
FIG. 4 shows an example a system that includes the dialysis machine and the gateway device in communication with the CH cloud in connection with use of a user feedback interface according to an implementation of the system described herein.

FIG. 4 is a schematic illustration of a system 400 that includes the dialysis machine 302 and the gateway device 310 in communication with the CH cloud 320 (e.g. shown as the connection 311) regarding use of a user feedback interface 450 according to an implementation of the system described herein. In some implementations, the gateway device 310 is a component of a connected health system for providing secure and controlled connectivity among components of the system to both internal and external networks and/or may be itself considered a part of the dialysis machine 302. For example, when the gateway device 310 is in communication with the dialysis machine 302, or when the gateway device 310 becomes associated with the dialysis machine 302 (e.g., when the gateway device 310 is first connected to or paired with the dialysis machine 302), the gateway device 310 may be considered part of the dialysis machine 302 and may be generally referred to as "belonging" to the dialysis machine 302.

The gateway device 310 is configured to communicate with the dialysis machine 302 (e.g. shown as the connection 301, such as a Bluetooth and/or WiFi connection). In this way, the gateway device 310 may act as a communications hub (e.g., node) that allows communication between the dialysis machine 302 and one or more other systems and/or devices. While the gateway device 310 is in wireless communication with the dialysis machine 302 in the illustrated example, the gateway device 310 and the dialysis machine 302 may also or alternatively be connected by a wired connection (e.g., an Ethernet cable). As described above, the gateway device 310 may also be connected, via the connection 311, to the external network/cloud 320.

According to an implementation of the system described herein, the gateway device 310 may include a control unit 410 (e.g., a processor and a memory device), connectivity components 420 (e.g. an antenna, transmitter and/or receiver etc.), a microphone 430, a speaker 440 and the user feedback interface 450, as further discussed in detail herein. The gateway device 310 is configured to receive audio input (e.g., spoken words, such as commands, questions/answers, etc.) through the microphone 430 and provide audio output (e.g., spoken words, such as questions/answers, instructions, alarms, alerts, confirmations, etc.) through the speaker 440. The control unit 410 is configured to process the audio input received through the microphone 430. The user feedback interface 450, shown in the illustrated example as one or more buttons disposed on the gateway device 310, may be engaged, as detailed herein, by a patient (or other user) 50 to enable the patient 50 to instantly provide user feedback. In an implementation, the user feedback interface 450 may be a button linked to the microphone on the gateway device 310 to record a patient's voice and upload it, via the connectivity components 420 and the connection 311 with the cloud 320, to the machine manufacturer to deliver instant feedback when the patient 50 wants to share it. In various implementations, this button may take the form of a physical button or a button in software on the gateway device 310.

In an implementation, when the patient 50 engages the instant user feedback interface 450, for example, by pressing an instant user feedback button on the gateway device 310, the patient 50 may be prompted by the system to provide the user feedback. The prompts may include automated questions audibly emitted from the gateway device 310 or other component, as further described in detail elsewhere herein. The patient's responses and other feedback may be transmitted over one or more networks using the connected health system 400 to a remote computer, server and/or location. At the same time as recording and/or transmitting the user feedback from the patient, the instant user feedback interface 450 may trigger the gathering of patient treatment and/or machine status information 460 from the dialysis machine 302 and/or any peripheral components connected thereto via the connection 301. This status information 460 may then be securely transmitted along with the user feedback information received from the patient 50 to the remote computer, server and/or location and thereby used to help understand the environment that caused the desire to provide user feedback. In one or more implementations, the status information 460 may include information about alarms on the dialysis machine 302, machine parameters, treatment details, status of supplies and/or other status information stored or available to the dialysis machine 302 at the time that the machine 302 is triggered via the user feedback interface 450 to provide the status information 460. Further, the user interface device 450 may allow the patient 50 to choose to whom the feedback is sent, such as the dialysis machine manufacturer and/or the patient's care team.

Figure 5:
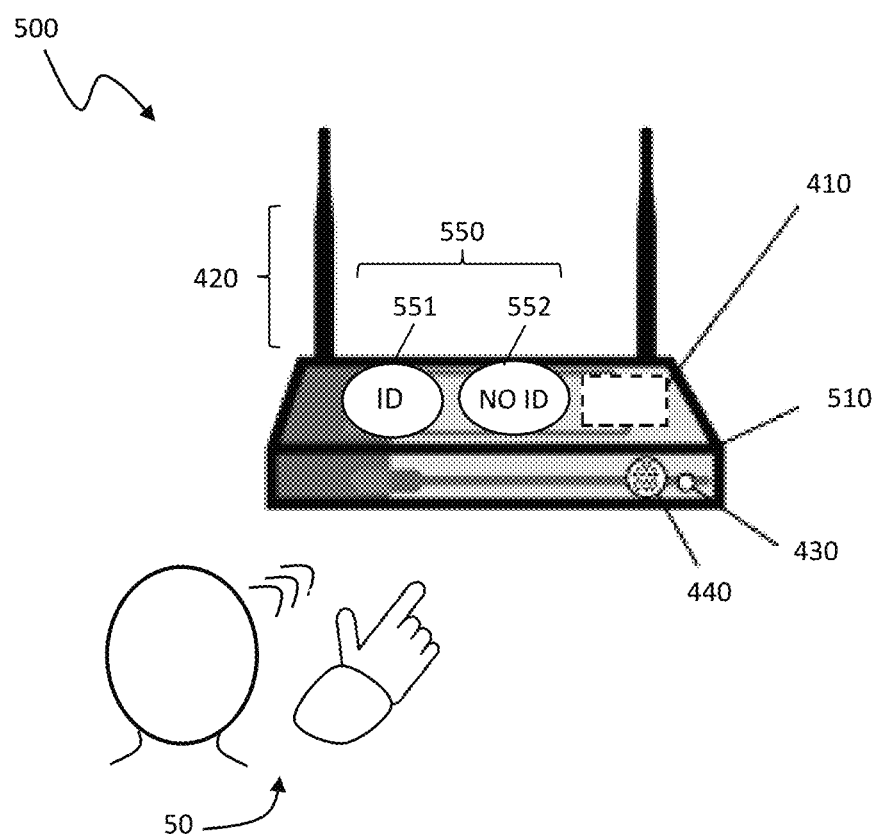
FIG. 5 is a schematic illustration showing another implementation of a user feedback system that includes a gateway device having another example of a user feedback device that includes multiple-option instant user feedback buttons.

FIG. 5 is a schematic illustration showing another implementation of a user feedback system 500 that includes a gateway device 510, similar to the gateway device 410, but including another example of a user feedback interface 550 that includes multiple-option instant user feedback buttons 551, 552. Specifically, in the illustrated example, the buttons 551, 552 may include the following: a button for providing feedback with an ID ("ID" button 551), and a button for providing feedback anonymously, without explicit identification ("NO ID" button 552).

For the feedback with ID option, e.g. after engaging the ID button 551, the patient 50 may provide voice feedback and information obtained in connection with the treatment for the patient 50. This information may include information provided by a fingerprint reader/patient card reader/keypad code entry/or electronic link of the dialysis machine 302 or gateway device 510 to the particular patient in the patient's medical record and may be securely transmitted along with the user feedback provided by the patient 50. The patient 50 who sends feedback using this method could expect some sort of follow-up, such as a phone call or an email response with a tracking number, to facilitate an issue resolution process. The interface 510 may allow or facilitate (via patient approval processing) the transmitting of dialysis machine status and/or patient treatment data/health status as part of the feedback to aid in machine learning and data analytics.

For the anonymous feedback option, e.g. engaging the NO ID button 552, the patient 50 may send voice feedback so that the patient 50 can express frustration, make suggestions, comment on current activity, etc. without the system providing explicit identification information along with the feedback. Accordingly, no follow-up would be provided or directly expected by the patient 50, aside from that identified as part of a safety protocol as noted below, and engaging the button 552 would simply provide a safe outlet for the patient 50 to be frank about their experiences. In this implementation, the patient 50 may not expect a direct response to the user feedback. As part of safety protocols, however, as noted by informational and disclaimer text concerning the user feedback system 500, operations may provide that identification of any emergency situation, such as machine status that affects safety and/or recognized words input by the patient 50 (e.g. "Help"), would cause transmitting of identification information regardless of the button 551 or the button 552 engaged by the patient 50. These options could be facilitated using the buttons 551, 552 and/or could be determined based on responsive input and output with the patient 50, e.g. further automated questions to the patient 50 and analyzing responses (e.g. "Yes" or "No") from the patient 50, as further described elsewhere herein.

In some implementations, the control unit 410 may transmit received user feedback, e.g. comments, questions, commands, to the CH cloud 320 for remote processing. The CH cloud 320 may then provide data to the control unit 410 that allows the control unit 410 to cause the speaker 440 to output audio output that responds or provides further information to the patient 50. In some implementation, the microphone 430 is configured to receive audio information (e.g., spoken information) as input from the patient 50. The control unit 410 can receive the audio information from the microphone 430 and identify one or more voice commands, questions, answers, etc. in the audio information. In some implementations, an audio message is presented by the speaker 440 if the spoken information is not understood or not permitted. For example, the speaker 440 may prompt the user to repeat themselves, or ask the user for clarification regarding the spoken information. In some implementations, the control unit 410 is configured to translate the audio information into text, e.g., for providing to the CH cloud 320 and/or to the dialysis machine 302.

In some implementations, the gateway device 310 may provide two-way conversational capability (e.g., back and forth communication) between the user and the gateway device 310. That is, the gateway device 310 may be configured to identify spoken words from the user, generate a spoken response based on the identified spoken words, receive a spoken response from the user, etc., in which each step of the spoken transaction is intelligently determined (e.g., by the gateway device 310 and/or one or more other devices/systems) based at least one previous spoken information. For example, after activating the user feedback interface 450 (e.g. pressing the button), the control unit 410 may cause the speaker 440 of the gateway device 310 to output audio that asks "How was your experience today?" The microphone 430 of the gateway device 310 may then be configured to receive expected audio input. The user can respond, for example, "It was ok." The gateway device 310 may then confirm and process the response identified. For example, the speaker 440 may say, "You said 'It was ok.' Would you like to provide user feedback?" The user might respond, "Yes," which the system would process and the system would then expect further audio input from the user to be transmitted as instant user feedback within the connected health system 300 according to the system described herein. The speaker 440 may also be used by the gateway device 310 to declare which button, ID 551 or No ID 552, has been pressed and the next expected action by the user, e.g. "You have pressed the No ID feedback button, all your comments will be kept confidential unless a safety issue arises, please speak after the tone," after which the microphone 430 would become active.

In some implementations, the gateway device 310 may provide information related to the spoken words identified in the audio information to one or more systems and/or devices (e.g., remote systems and/or devices) via the CH cloud 320, and the one or more systems and/or devices may assist in determining an action to be performed based on the identified spoken words. For example, the feedback with ID button 551 could be then further used for ordering supplies, like keeping a running tab, e.g. enabling voice feedback of: "I just used an extra solution bag because one was leaking." The system may then respond "Would you like to order additional solutions bags?" and await a response from the patient 50. Based on the response from the patient 50, resulting actions taken to respond to those voice input instructions. Status information provided from the dialysis machine 302 may be used to confirm details of the issue, e.g. the type of solution bags that are needed to be resupplied and that information transmitted along with the user feedback.

Figure 6:
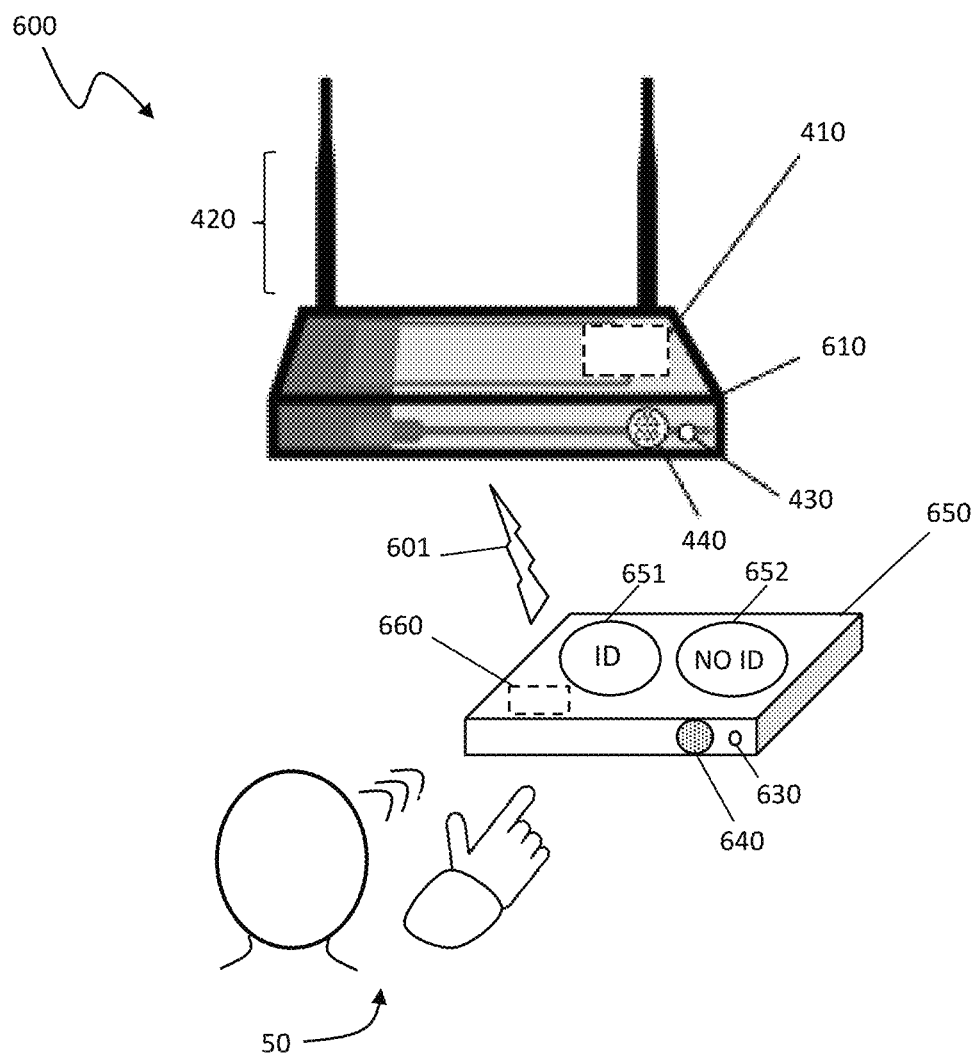
FIG. 6 is a schematic illustration showing another implementation of a user feedback system that includes a gateway device including a user feedback device that is separate or remote from the gateway device.

FIG. 6 is a schematic illustration showing another implementation of a user feedback system 600 that includes a gateway device 610, similar to the gateway device 410 and/or the gateway device 510, but further including a user feedback device 650 that is separate or remote from the gateway device 610. The user feedback device 650 includes multiple-option instant user feedback buttons 651, 652, that may function like those of the buttons 551, 552 discussed above in connection with the user feedback system 500. In an implementation, the separate user feedback device 650 may be on a same local network as the gateway device 610, such as the same WiFi and/or Bluetooth network that is represented by the connection 301 discussed above, and may be in wireless communication with the gateway device 610, which is illustrated as the connection 601 in the figure. The user feedback device 650 may further include a microphone 630, a speaker 640 and a processor 660 that enables the device 650 to receive voice input from the user, process into a transmittable form and transmit that information wirelessly, via the connection 601, to the gateway device 610 for further processing and transmission similar to that discussed elsewhere herein, for example, like that described in connection with operations of the gateway device 510. In another implementation, the user feedback device 650 may be configured for connection directly to the external network and enabled to, in some circumstances, transmit information directly over the external network, such as via a mobile telecommunications network.

Figure 7:
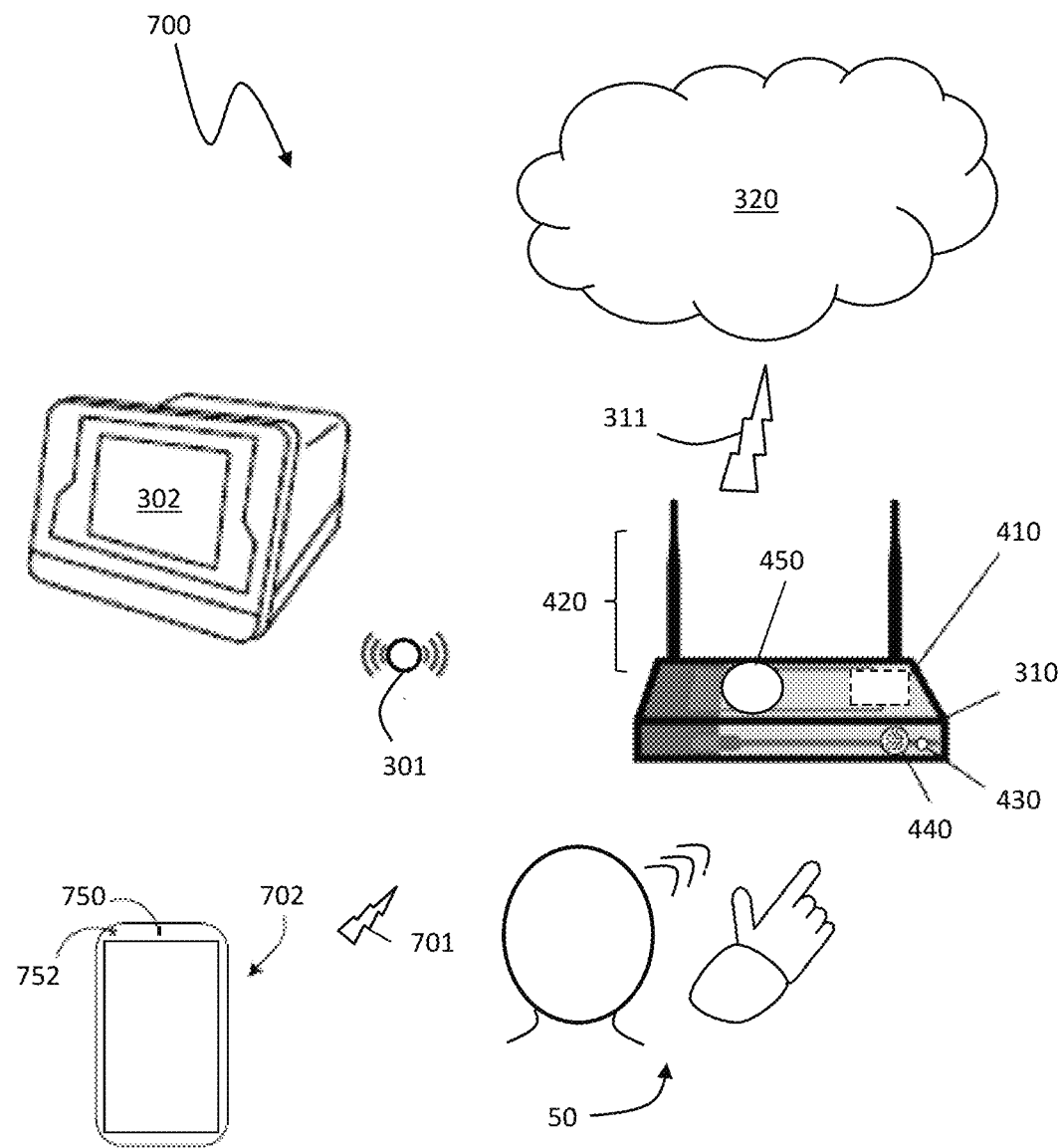
FIG. 7 is a schematic illustration showing an example of a system that includes the dialysis machine, the gateway device, and a mobile computing device according to an implementation of the system described herein.

FIG. 7 is a schematic illustration showing an example of a system 700 that includes the dialysis machine 302, the gateway device 310, and a mobile computing device 702 of the patient 50 according to an implementation of the system described herein. The mobile computing device 702 is in communication (e.g., wired or wireless communication) with one or more of the dialysis machine 302, the gateway device 310, and the CH cloud 320. In the illustrated example, the mobile computing device 702 is a mobile phone or smartphone, but other mobile computing devices may also or alternatively be used, such tablet computers, laptop computers, etc. The mobile computing device 702 includes a microphone 750 and a speaker 752 and is configured to provide voice interface capability substantially as described above. In some implementations, the gateway device 310 of the system 700 may omit the microphone 430 and/or the speaker 440, and the voice recognition capabilities and two-way conversational capabilities may be handled by the mobile computing device 702 (e.g., an application running on the mobile computing device). In this way, the mobile computing device 702 may serve as a communication conduit between the dialysis machine 302 and the CH cloud 320, or between the dialysis machine 302, the gateway device 310, and/or the CH cloud 320.

Additionally, the instant user feedback interface 450 of the gateway device 310 may include a feature to instantly link to the patient's mobile computing device 702 using Bluetooth, NFC or other short range wireless protocol. In one or more implementations, the instant link feature of the instant user feedback interface 450 may be activated automatically when the user feedback interface 450 is manually activated and the patient's smartphone 750 is in proximity to the user feedback interface 450 and/or the gateway device 310. Additionally and/or alternatively, the patient 50 may be prompted and/or otherwise instructed as to whether instant linking is desired. For example, pressing the user feedback interface 450 twice may activate the instant link features and/or an audible request may be initiated by the user feedback interface 450 ("Do you want to link your mobile phone?") and a response expected from the patient 50. If the patient 50 wants to provide photo or video with the feedback, use of the instant link interface feature allows the next video or picture taken to be transmitted along with the user feedback, and which may simplify the sharing process for less tech-savvy patients. The picture taking feature may further be used to capture equipment QR/bar codes for traceability to particular products. If the picture appears blurry or unreadable, the system 700 may ask the patient 50 to retake the picture. A more advanced implementation may allow the patient to save the user feedback for later review and editing, and to attach media before sending. This may be accomplished by automatically linking to the patient's smartphone/tablet 750 and packaging the feedback as a draft text message/email/app message addressed to the desired party. The patient 50 may press the send button when ready to provide the user feedback and media (image, video etc.).

Figure 8:
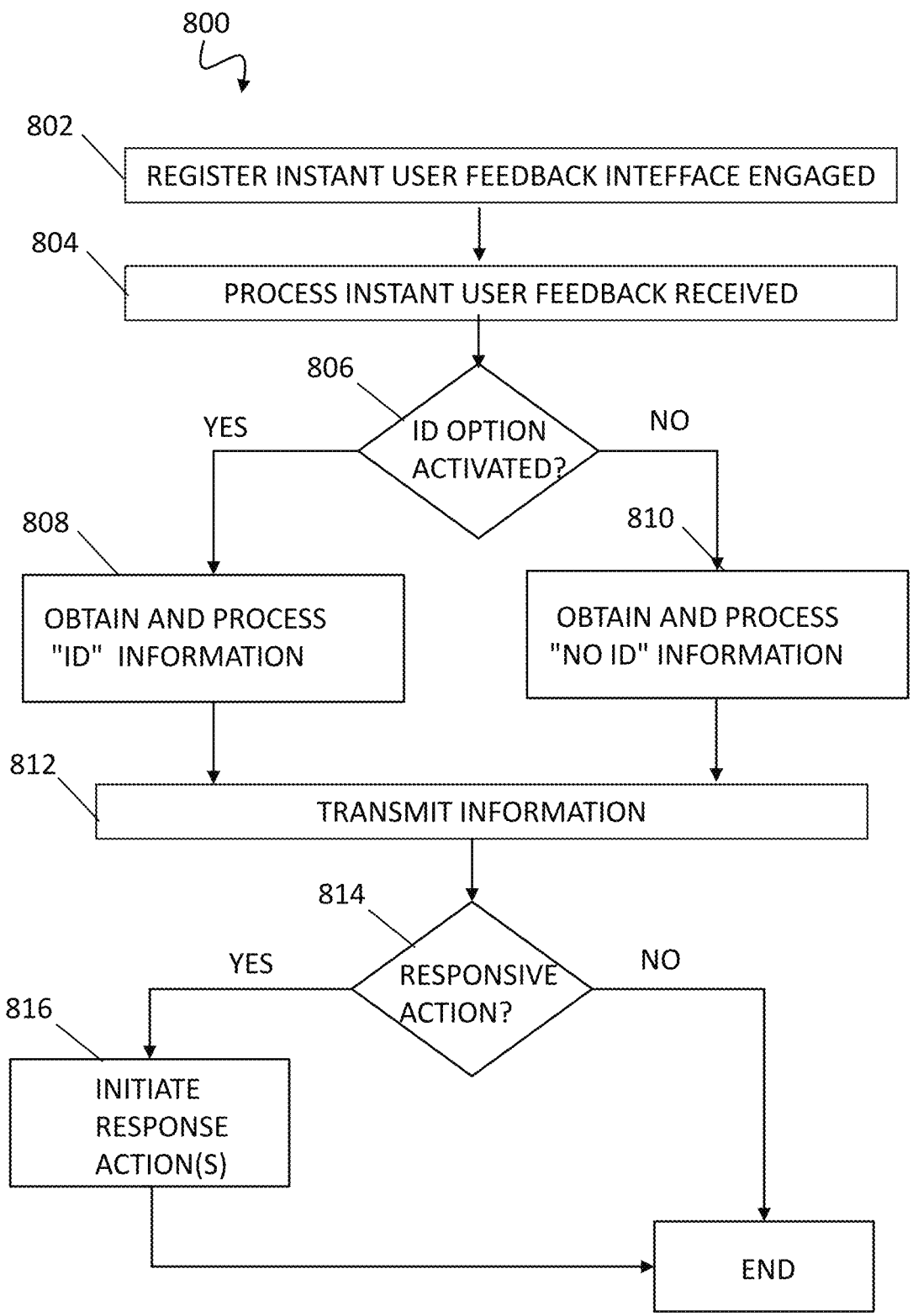
FIG. 8 is a flow diagram showing flow processing for a process iteration of receiving, processing and transmitting user feedback via an instant user feedback interface for a connected health system having components as discussed herein in connection with one or more implementations of instant user feedback interfaces.

FIG. 8 is a flow diagram 800 showing flow processing for a process iteration of receiving, processing and transmitting user feedback via an instant user feedback interface for a connected health system having components as discussed herein in connection with one or more implementations of instant user feedback interfaces. At a step 802, the instant user feedback interface is engaged by a patient. For example, the patient presses a button on a gateway device of the connected health system and/or on a separate user feedback interface device linked to the gateway device. At a step 804, the instant user feedback is processed, which may include recording the voice input of the patient using the gateway device and/or using a separate user interface device and transmitting the voice input user feedback information to the gateway device. This step 804 may include processing to indicate to whom the patient desires the information to be transmitted, as well as linking processing to a patient's smartphone to enable capture and processing of other media (images, video) besides the patient's voice input, as described above. This step 804 may also include further exchanges with the patient in an implementation in which two-way conversational capability and/or other input and response information is exchanged between the patient and the user interface device.

At a decision step 806, it is determined whether an identification option of the patient that is provided by the user interface feedback interface has been activated by the patient. For example, the instant user feedback interface may include an "ID" button that is pressed by the patient to provide user feedback with patient identification information to be provided and corresponding responsive action expected. Otherwise the patient may press the "NO ID" button and thereby not expect a specific responsive action to be taken. If the "ID" button has been pressed (being a YES at the decision step 806), then processing proceeds to a step 808 where corresponding information is obtained. This may include obtaining patient identification information, treatment identification, machine status information and/or other types of information. If the "NO ID" button has been pressed (being a NO at the decision step 806), then processing proceeds to a step 810 where corresponding information is obtained. This may include information corresponding to safety protocols, which may include machine status information and some level of patient identification information that would enable identification in the event of an emergency, among other information. It is noted that the system default, for example, where there are no identification options provided (i.e. where there is only one instant user feedback button) may be the "ID" option processing of the step 808.

After either the steps 808 or 810, processing proceeds to a step 812 where the received user feedback information and the corresponding status information are transmitted via the connected health system to a remote location. The remote location may include a remote computer, server, clinic, company headquarters site and/or other type of remote location where the user feedback information and the status information may be processed. Processing may include recording, tabulating, analyzing the user feedback information and status information received, including for purposes of improving customer experience and/or product improvement. At a decision step 814, it is determined whether a responsive action is needed. The step 814 may include processing to determine if a responsive action is needed, such as whether there was an emergency health or machine status situation that needs resolving. The processing may also include processing the user feedback information to determine if a responsive customer service action is needed to respond to the user feedback. If responsive action is needed (being a YES at the step 814), then processing proceeds to a step 816 where a response action is initiated. After the step 816, processing is ended for the iteration of user feedback interface processing being described. If responsive action is not needed (being a NO at the step 814), then processing is ended for the iteration of user feedback interface processing being described.

Embodiments or implementations discussed herein may be combined with each other in appropriate combinations in connection with the system described herein. Additionally, in some instances, the order of steps in the flow diagrams, flowcharts and/or described flow processing may be modified, where appropriate. The system may further include a display and/or other computer components for providing a suitable interface with a user and/or with other computers. Aspects of the system described herein may be implemented or controlled using software, hardware, a combination of software and hardware and/or other computer-implemented or computer-controlled modules or devices having described features and performing described functions. Data exchange and/or signal transmissions to, from and between components of the system may be performed using wired or wireless communication. This communication may include use of one or more transmitter or receiver components that securely exchange information via a network, such as the Internet, and may include use of components of local area networks (LANs) or other smaller scale networks, such as Wi-Fi, Bluetooth or other short range transmission protocols, and/or components of wide area networks (WANs) or other larger scale networks, such as mobile telecommunication networks.

Software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media, an SD card, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system. The meanings of any method steps of the invention(s) described herein are intended to include any suitable method of causing one or more parties or entities to perform the steps unless a different meaning is expressly provided or otherwise clear from the context.

As used herein, an element or operation recited in the singular and preceded with the word "a" or "an" should be understood as not excluding plural elements or operations, unless such exclusion is explicitly recited. References to "one" embodiment or implementation of the present disclosure are not intended to be interpreted as excluding the existence of additional embodiments that also incorporate the recited features. Furthermore, a description or recitation in the general form of "at least one of [a], [b] or [c]," or equivalent thereof, should be generally construed to include [a] alone, [b] alone, [c] alone, or any combination of [a], [b] and [c].

Embodiments and implementations of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. An instant user feedback system for a medical device in a home, comprising:
    a gateway device configured to connect to a local network within the home and configured to connect to a remote network that is external to the home;
    a microphone configured to receive voice input from a user;
    an instant user feedback interface communicatively coupled to the gateway device, wherein, when engaged, the instant user feedback interface activates the microphone to receive the voice input from the user;
    wherein the gateway device includes a control unit, the control unit configured to:
        process the voice input into transmissible user feedback information;
        obtain status information of the medical device via the local network; and
        transmit the user feedback information and the status information to a remote system via the external network, and
    wherein the instant user feedback interface includes two buttons that present two options to the user, wherein a first option of the two options is an identification option that indicates user identification information will be transmitted identifying the user, and wherein a second option of the two options is a non-identification option that indicates limited user identification information will be transmitted.

2. The instant user feedback system of claim 1, wherein the medical device is a dialysis machine.

3. The instant user feedback system of claim 1, wherein the two buttons of the instant user feedback interface are on the gateway device.

4. The instant user feedback system of claim 1, wherein the two buttons of the instant user feedback interface are on a user feedback device that is remote from the gateway device and that communicates with the gateway device.

5. The instant user feedback system of claim 1, wherein the gateway device comprises a speaker configured to output spoken words to the user.

6. The instant user feedback system of claim 5, wherein the gateway device is configured to provide two-way conversational capability between the user and the gateway device.

7. The instant user feedback system of claim 1, wherein the non-identification option includes safety protocol information that enables emergency condition identification of the user.

8. The instant user feedback system of claim 1, wherein, a responsive action in response to the user feedback information is determined at the remote system, and wherein the instant user feedback system receives information on the responsive action from the remote system.

9. The instant user feedback system of claim 1, further comprising a mobile computing device of the user that couples to the gateway device when brought into proximity to the gateway device and that is configured to provide an image or a video to the gateway device related to the voice input.

10. A medical system, comprising:
    a medical device disposed in a home of a user;
    an instant user feedback system for the medical device, the instant user feedback system comprising:
        a gateway device configured to connect to a local network within the home and configured to connect to a remote network that is external to the home;
        a microphone configured to receive voice input from a user;
        an instant user feedback interface communicatively coupled to the gateway device, wherein, when engaged, the instant user feedback interface activates the microphone to receive the voice input from the user;
        wherein the gateway device includes a control unit, the control unit configured to:
            process the voice input into transmissible user feedback information;
            obtain status information of the medical device via the local network; and
            transmit the user feedback information and the status information to a remote system via the external network, and
        wherein the instant user feedback interface includes two buttons that present two options to the user, wherein a first option of the two options is an identification option that indicates user identification information will be transmitted identifying the user, and wherein a second option of the two options is a non-identification option that indicates limited user identification information will be transmitted.

11. The medical system of claim 10, wherein the medical device is a dialysis machine.

12. The medical system of claim 10, wherein the two buttons of the instant user feedback interface are on the gateway device.

13. The medical system of claim 10, wherein the two buttons of the instant user feedback interface are on a user feedback device that is remote from the gateway device and that communicates with the gateway device.

14. The medical system of claim 10, wherein the gateway device comprises a speaker configured to output spoken words to the user.

15. The medical system of claim 14, wherein the gateway device is configured to provide two-way conversational capability between the user and the gateway device.

16. The medical system of claim 10, wherein the non-identification option includes safety protocol information that enables emergency condition identification of the user.

17. The medical system of claim 10, wherein, a responsive action in response to the user feedback information is determined at the remote system, and wherein the instant user feedback system receives information on the responsive action from the remote system.

18. The medical system of claim 10, further comprising a mobile computing device of the user that couples to the gateway device when brought into proximity to the gateway device and that is configured to provide an image or a video to the gateway device related to the voice input.

\* \* \* \* \*